United States Patent [19]

May et al.

[11] 4,389,403
[45] Jun. 21, 1983

[54] 1-AROYL-2-PHENYLAMINO-2-IMIDAZO-LINES, DRUGS CONTAINING THESE COMPOUNDS, AND USE THEREOF

[75] Inventors: Hans-Joachim May, Neustadt; Dieter Lenke, Ludwigshafen; Josef Gries, Wachenheim; Hans-Juergen Teschendorf, Ludwigshafen; Wolfgang Worstmann, Hiltrup, all of Fed. Rep. of Germany

[73] Assignee: BASF Aktiengesellschaft, Fed. Rep. of Germany

[21] Appl. No.: 240,111

[22] Filed: Mar. 3, 1981

[30] Foreign Application Priority Data

Mar. 24, 1980 [DE] Fed. Rep. of Germany ....... 3011327

[51] Int. Cl.³ .................. A61K 31/415; A61K 31/47; C07D 401/06
[52] U.S. Cl. .................................... 424/258; 424/250; 424/263; 424/266; 424/270; 424/272; 424/273 R; 544/235; 544/405; 546/145; 546/146; 546/168; 546/278; 548/136; 548/141; 548/143; 548/144; 548/200; 548/214; 548/236; 548/248; 548/316
[58] Field of Search ............... 548/136, 141, 144, 143, 548/200, 214, 236, 248, 316; 544/235, 405; 546/145, 146, 168, 278; 424/250, 258, 263, 266, 270, 272, 273

[56] References Cited

U.S. PATENT DOCUMENTS 4,269,990 5/1981 May et al. ......................... 548/316

FOREIGN PATENT DOCUMENTS 2505297 10/1975 Fed. Rep. of Germany .
2559711 9/1977 Fed. Rep. of Germany .

Primary Examiner—Robert W. Ramsuer
Attorney, Agent, or Firm—Keil & Witherspoon

[57] ABSTRACT

1-Aroyl-2-phenylamino-2-imidazolines of the general formula

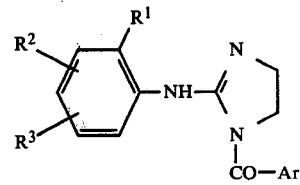

where
$R^1$ and $R^2$ are identical or different and each is chlorine, bromine, fluorine, methyl, ethyl, methoxy, trifluoromethyl or cyano,
$R^3$ has the meanings given for $R^1$ and $R^2$ or is hydrogen and
Ar is an unsubstituted or substituted monocyclic or bicyclic heteroaromatic radical containing 1, 2 or 3 nitrogen and/or oxygen and/or sulfur atoms, their salts with physiologically tolerated acids, their preparation, and drugs containing these compounds.

The compounds have, inter alia, a blood pressure-reducing action.

14 Claims, No Drawings

1-AROYL-2-PHENYLAMINO-2-IMIDAZOLINES, DRUGS CONTAINING THESE COMPOUNDS, AND USE THEREOF

The present invention relates to novel 1-aroyl-2-phenylamino-2-imidazolines, processes for their preparation, drugs which contain the novel compounds, and their use in the treatment of hypertonia, migraine and coronary heart disease.

German Published Application DAS No. 2,559,711 discloses that benclonidine (1-benzoyl-2-(2',6'-dichlorophenylamino)-2-imidazoline), like clonidine (2-(2',6'-dichlorophenylamino)-2-imidazoline), exhibits blood pressure-reducing properties. The compound is alleged to have lesser sedative side-effects than the parent compound clonidine, and to be efficiently absorbed on oral administration.

Furthermore, German Laid-Open Application DOS No. 2,505,297 describes not only the 1-benzoyl derivative of clonidine but also the 3 isomeric toluoyl derivatives, which allegedly have a similar ratio of blood pressure-reducing action to sedative action.

We have found compounds having more advantageous properties.

The present invention relates to 1-aroyl-2-phenylamine-2-imidazolines of the general formula I

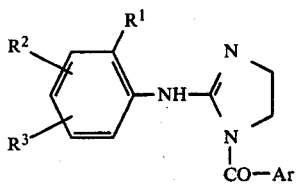

where
R$^1$ and R$^2$ are identical or different and each is chlorine, bromine, fluorine, methyl, ethyl, methoxy, trifluoromethyl or cyano,
R$^3$ has the meanings given for R$^1$ and R$^2$ or is hydrogen and
Ar is an unsubstituted or substituted monocyclic or bicyclic heteroaromatic radical containing 1, 2 or 3 nitrogen and/or oxygen and/or sulfur atoms, and their salts with physiologically tolerated acids.

Examples of monocyclic heteroaromatic radicals are pyrrolyl, furyl, thienyl, imidazolyl, oxazolyl, isoxazolyl, thiazolyl, isothiazolyl, oxadiazolyl, thiadiazolyl, pyridyl and pyrazinyl; examples of bicyclic heteroaromatic radicals are indolyl, benzfuranyl, quinolinyl, isoquinolinyl, cinnolinyl, benzodioxolyl and benzodioxanyl. Ar may be substituted by one or more of the following radicals: alkyl of 1 to 6 carbon atoms (eg. methy, ethyl, n-propyl, i-propyl, n-butyl, n-pentyl or n-hexyl), which can in turn be substituted by halogen, hydroxyl or alkoxy of 1 to 4 carbon atoms (eg. haloethyl, halopropyl, halobutyl, hydroxyethyl, hydroxypropyl, hydroxybutyl, alkoxymethyl, alkoxyethyl, alkoxypropyl or alkoxybutyl), halogen (eg. fluorine, chlorine or bromine), hydroxyl, alkoxy of 1 to 6 carbon atoms (eg. methoxy, ethoxy, propoxy, butoxy, pentoxy or hexoxy) or alkylmercapto of 1 to 4 carbon atoms (eg. methylmercapto, ethylmercapto, propylmercapto or butylmercapto). If the heteroaromatic radical contains nitrogen, the latter may also be substituted by oxygen, ie. the compound may be in the form of the N-oxide.

Examples of preferred radicals R$^1$ are chlorine, bromine, fluorine, methyl, cyano and trifluoromethyl.

Very particularly preferred substituent combinations R$^1$ and R$^2$ are 2,6-dihalo, eg. 2,6-dichloro, 2-chloro-6-bromo and 2,6-dibromo, 2-fluoro-6-trifluoromethyl and 2-chloro-3-methyl, 2-chloro-4-methyl and 2-methyl-5-fluoro.

Amongst the meanings of Ar, the following unsubstituted radicals are preferred: furyl, thienyl, pyridyl, pyrazinyl, benzodioxolyl, benzodioxanyl, quinolinyl and isoquinolinyl. Preferred substituted radicals Ar are fluoropyridyl, methylpyridyl, methylquinolinyl, methoxyquinolinyl, trifluoromethylquinolinyl and fluoroquinolinyl. Very particularly preferred radicals Ar are 3-pyridyl, 2-quinolinyl and 1-isoquinolinyl.

The present invention furthermore relates to a process for the preparation of the compounds of the formula I, wherein
(a) an amine of the formula II

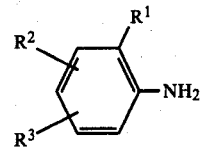

where R$^1$, R$^2$ and R$^3$ have the above meanings, is reacted with a 1-aroyl-2-imidazolidinone of the formula III

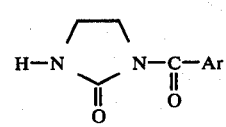

where Ar has the above meanings in the presence of not less than 1 mole of phosphorus oxytrichloride, at from 20° to 120° C., or
(b) the activated derivative of an alkylcarboxylic acid of the formula IV

where Ar has the same meanings as above, is reacted with a 2-arylamino-2-imidazoline of the formula V

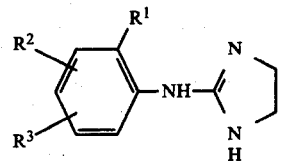

where R$^1$, R$^2$ and R$^3$ have the same meanings as above, and, if desired, the resulting compound is converted to a salt with a physiologically tolerated acid.

The reaction of the amine II with a 1-aroyl-2-imidazolidinone III, according to a), is preferably carried out with a molar ratio of from 1:1.1 to 1:1.5, and furthermore advantageously in excess POCl$_3$ as the solvent, preferably at from 40° to 70° C. or at the reflux temperature of any solvent which may be used. The reaction can also advantageously be carried out in the presence of an inert organic solvent, for example a chlorohydrocarbon, eg. chloroform or carbon tetrachloride.

Furthermore, because the amine used is relatively easily oxidized, it is advantageous to carry out the reaction in an inert atmosphere, for example under nitrogen or argon.

When the reaction, which can be followed by, for example, thin layer chromatography, is complete, the excess POCl$_3$ is removed by distillation, and after neutralizing the residue the novel compounds I obtained are purified, if required, by physical methods, for example partitioning, crystallization or chromatography, or by chemical methods, for example formation of salts, crystallization of these and their subsequent decomposition in alkaline media. In carrying out the purification, the nature of the anion in the salt is immaterial, since all that matters is that the salt should be well-defined and easily crystallizable.

The excess POCl$_3$ is preferably distilled off, advantageously under reduced pressure so as not to damage the product. Cold water, preferably ice water, is added to the distillation residue, and the mixture is rendered distinctly alkaline with an aqueous alkaline solution, for example a sodium bicarbonate, sodium carbonate or sodium hydroxide solution, and is extracted with a water-immiscible solvent, such as methylene chloride or chloroform. After removing the solvent, the novel substance I is preferably purified by crystallization from an inert organic solvent, for example hexane, cyclohexane, toluene, isopropanol or acetonitrile.

The 1-aroyl-2-imidazolidinones of the formula III, used as starting materials, have not previously been disclosed. They may be obtained in a conventional manner, and in good yield, by acylating ethyleneurea with an arylcarboxylic acid anhydride or an arylcarboxylic acid halide, in the presence or absence of an acid acceptor, for example triethylamine, pyridine or antipyrine.

Examples of suitable activated alkylcarboxylic acid derivatives for process b) are azolides containing a heterocyclic quasi-aromatic five-membered ring with not less than two nitrogen atoms, for example imidazole, pyrazole, 1,2,3-triazole, 1,2,4-triazole, 1,2,4-oxdiazole, tetrazole, benzimidazole, benztriazole and their substitution products.

Amongst the azolides, the imidazolides are particularly preferred, because of being easily obtainable and cheap. They can be prepared in virtually quantitative yield by conventional methods, either by reacting an arylcarboxylic acid with an N,N'-carbonyldiimidazole or N,N'-thiocarbonyldiimidazole or by reacting an arylcarboxylic acid chloride with imidazole in a molar ratio of 1:2. Their further reaction with the imidazolines of the formula V is carried out by the conventional methods for transacylation reactions of imidazolides.

An advantageous procedure is to react the free arylcarboxylic acid with an N,N'-carbonyldiimidazole in a molar ratio of 1:1 at room temperature in an inert solvent and to add the imidazoline V when the evolution of CO$_2$ has ceased. The reaction time depends on the reactivity of the imidazolide. As a rule, however, the reaction is complete after 1-2 hours at room temperature, though, if necessary, the mixture can be heated, at most to the boiling point of the solvent used. Examples of suitable solvents are methylene chloride, chloroform, benzene, toluene, xylene, tetrahydrofuran, dioxane, N,N'-dimethylacetamide, N-methylpyrrolidin-2-one, 1,3-dimethyl-imidazolidin-2-one, 1,3-dimethyl-3,4,5,6-tetrahydro-2(1H)-pyrimidinone, N,N'-dimethylformamide, hexamethylphosphorotriamide, dimethylsulfoxide, acetonitrile or mixtures of these. Working up is carried out in a conventional manner appropriate to the solvent used. The substances according to the invention can either be precipitated in a crystalline form by directly adding to the reaction mixture an aqueous alkaline solution, for example a sodium bicarbonate, sodium carbonate or sodium hydroxide solution, until the pH is 8, or be isolated in a similar manner after first removing the solvent and, where appropriate, extracting the mixture with a solvent.

The following are examples of compounds which may be obtained by processes 1 and 2: 1-(pyrrol-2-oyl)-2-(2',6'-dichlorophenylamino)-2-imidazoline, 1-(1-methyl-pyrrol-2-oyl)-2-(2',6'-dichlorophenylamino)-2-imidazoline, 1-(fur-2-oyl)-2-(2',6'-dichlorophenylamino)-2-imidazoline, 1-(fur-3-oyl)-2-(2',6'-dichlorophenylamino)-2-imidazoline, 1-(5-methyl-fur-2-oyl)-2-(2',6'-dichlorophenylamino)-2-imidazoline, 1-(then-2-oyl)-2-(2',6'-dichlorophenylamino)-2-imidazoline, 1-(then-3-oyl)-2-(2',6'-dichlorophenylamino)-2-imidazoline, 1-(3-methyl-then-2-oyl)-2-(2',6'-dichlorophenylamino)-2-imidazoline, 1-(5-methyl-then-2-oyl)-2-(2',6'-dichlorophenylamino)-2-imidazoline, 1-(2-methyl-imidazol-5-oyl)-2-(2',6'-dichlorophenylamino)-2-imidazoline, 1-(4-methylimidazol-5-oyl)-2-(2',6'-dichlorophenylamino)-2-imidazoline, 1-(oxazol-4-oyl)-2-(2',6'-dichlorophenylamino)-2-imidazoline, 1-(4-methyl-oxazol-5-oyl)-2-(2',6'-dichlorophenylamino)-2-imidazoline, 1-(5-methyl-isoxazol-3-oyl)-2-(2',6'-dichlorophenylamino)-2-imidazoline, 1-(5-methyl-isoxazol-4-oyl)-2-(2',6'-dichlorophenylamino)-2-imidazoline, 1-(3-methyl-isoxazol-5-oyl)-2-(2',6'-dichlorophenylamino)-2-imidazoline, 1-(2-methyl-thiazol-4-oyl)-2-(2',6'-dichlorophenylamino)-2-imidazoline, 1-(2-methyl-thiazol-5-oyl)-2-(2',6'-dichlorophenylamino)-2-imidazoline, 1-(2-propyl-thiazol-5-oyl)-2-(2',6'-dichlorophenylamino)-2-imidazoline, 1-(2-butyl-thiazol-5-oyl)-2-(2',6'-dichlorophenylamino)-2-imidazoline, 1-(isothiazol-4-oyl)-2-(2',6'-dichlorophenylamino)-2-imidazoline, 1-(2-methyl-1,3,4-oxidazol-5-oyl)-2-(2',6'-dichlorophenylamino)-2-imidazoline, 1-(2-methylmercapto-1,3,4-oxidazol-5-oyl)-2-(2',6'-dichlorophenylamino)-2-imidazoline, 1-(2-methyl-1,3,4-thiadiazol-5-oyl)-2-(2',6'-dichlorophenylamino)-2-imidazoline, 1-(2-methylmercapto-1,3,4-thiadiazol-5-oyl)-2-(2',6'-dichlorophenylamino)-2-imidazoline, 1-(pyrid-2-oyl)-2-(2',6'-dichlorophenylamino)-2-imidazoline, 1-(pyrid-3-oyl)-2-(2',6'-dichlorophenylamino)-2-imidazoline, 1-(pyrid-4-oyl)-2-(2',6'-dichlorophenylamino)-2-imidazoline, 1-(3-methyl-pyrid-2-oyl)-2-(2',6'-dichlorophenylamino)-2-imidazoline, 1-(4-methyl-pyrid-2-oyl)-2-(2',6'-dichlorophenylamino)-2-imidazoline, 1-(5-methyl-pyrid-2-oyl)-2-(2',6'-dichlorophenylamino)-2-imidazoline, 1-(6-methyl-pyrid-2-oyl)-2-(2',6'-dichlorophenylamino)-2-imidazoline, 1-(N-oxido-6-methyl-pyrid-2-oyl)-2-(2',6'-dichlorophenylamino)-2-imidazoline, 1-(5-n-propyl-pyrid-2-oyl)-2-(2',6'-dichlorophenylamino)-2-imidazoline, 1-(5-(n-butyl)-pyrid-2-oyl)-2-(2',6'-dichlorophenylamino)-2-imidazoline, 1-(5-(3-chloropropyl)-pyrid-2-oyl)-2-(2',6'-dichlorophenylamino)-2-imidazoline, 1-(5-(3-methoxypropyl)-pyrid-2-oyl)-2-(2',6'-dichlorophenylamino)-2-imidazoline, 1-(5-methoxy-pyrid-2-oyl)-2-(2',6'-dichlorophenylamino)-2-imidazoline, 1-(5-propoxypyrid-2-oyl)-2-(2',6'-dichlorophenylamino)-2-imidazoline, 1-(2-methyl-pyrid-3-oyl)-2-(2',6'-dichlorophenylamino)-2-imidazoline, 1-(4-methyl-pyrid-3-oyl)-2-(2',6'-dichlorophenylamino)-2-imidazoline, 1-(5-methyl-pyrid-3-oyl)-2-(2',6'-dichlorophenylamino)-2- imidazoline, 1-(6-methyl-pyrid-3-oyl)-2-(2',6'-dichlorophenylamino)-2-imidazoline, 1-(2,4-dimethyl-pyrid-3-oyl)-2-(2',6'-dichlorophenylamino)-2-imidazoline, 1-(2,6-dimethylpyrid-3-oyl)-2-(2',6'-dichlorophenylamino)-2-imidazoline, 1-(5,6-dimethyl-pyrid-3-oyl)-2-(2',6'-dichlorophenylamino)-2-imidazoline, 1-(5-fluoro-pyrid-3-oyl)-2-(2',6'-dichlorophenylamino)-2-imidazoline, 1-(6-fluoro-pyrid-3-oyl)-2-(2',6'-dichlorophenylamino)-2-imidazoline, 1-(6-chloro-pyrid-3-oyl)-2-(2',6'-dichlorophenylamino)-2-imidazoline, 1-(6-hydroxy-pyrid-3-oyl)-2-(2',6'-dichlorophenylamino)-2-imidazoline, 1-(2-methoxy-pyrid-3-oyl)-2-(2',6'-dichlorophenylamino)-2-imidazoline, 1-(2-methyl-pyrid-4-oyl)-2-(2',6'-dichlorophenylamino)-2-imidazoline, 1-(3-methyl-pyrid-4-oyl)-2-(2',6'-dichlorophenylamino)-2-imidazoline, 1-(2-fluoro-pyrid-4-oyl)-2-(2',6'-dichlorophenylamino)-2-imidazoline, 1-(2,6-dimethyl-pyrid-4-oyl)-2-(2',6'-dichlorophenylamino)-2-imidazoline, 1-(N-oxido-pyrid-4-oyl)-2-(2',6'-dichlorophenylamino)-2-imidazoline, 1-(pyrazin-2-oyl)-2-(2',6'-dichlorophenylamino)-2-imidazoline, 1-(indol-2-oyl)-2-(2',6'-dichlorophenylamino)-2-imidazoline, 1-(1-methylindol-2-oyl)-2-(2',6'-dichlorophenylamino)-2-imidazoline, 1-(indol-3-oyl)-2-(2',6'-dichlorophenylamino)-2-imidazoline, 1-(indol-5-oyl)-2-(2',6'-dichlorophenylamino)-2-imidazoline, 1-(benzofur-5-oyl)-2-(2',6'-dichlorophenylamino)-2-imidazoline, 1-(quinolin-2-oyl)-2-(2',6'-dichlorophenylamino)-2-imidazoline, 1-(quinolin-3-oyl)-2-(2',6'-dichlorophenylamino)-2-imidazoline, 1-(quinolin-4-oyl)-2-(2',6'-dichlorophenylamino)-2-imidazoline, 1-(isoquinolin-1-oyl)-2-(2',6'-dichlorophenylamino)-2-imidazoline, 1-(isoquinolin-3-oyl)-2-(2',6'-dichlorophenylamino)-2-imidazoline, 1-(4-methyl-quinolin-2-oyl)-2-(2',6'-dichlorophenylamino)-2-imidazoline, 1-(5-methylquinolin-2-oyl)-2-(2',6'-dichlorophenylamino)-2-imidazoline, 1-(6-methyl-quinolin-2-oyl)-2-(2',6'-dichlorophenylamino)-2-imidazoline, 1-(7-methyl-quinolin-2-oyl)-2-(2',6'-dichlorophenylamino)-2-imidazoline, 1-(6-methoxy-quinolin-2-oyl)-2-(2',6'-dichlorophenylamino)-2-imidazoline, 1-(6-trifluoromethyl-quinolin-2-oyl)-2-(2',6'-dichlorophenylamino)-2-imidazoline, 1-(7-trifluoromethyl-quinolin-2-oyl)-2-(2',6'-dichlorophenylamino)-2-imidazoline, 1-(3-methyl-isoquinolin-1-oyl)-2-(2',6'-dichlorophenylamino)-2-imidazoline, 1-(5-fluoroquinolin-2-oyl)-2-(2',6'-dichlorophenylamino)-2-imidazoline, 1-(6-fluoro-quinolin-2-oyl)-2-(2',6'-dichlorophenylamino)-2-imidazoline, 1-(7-fluoro-quinolin-2-oyl)-2-(2',6'-dichlorophenylamino)-2-imidazoline, 1-(cinnolin-4-oyl)-2-(2',6'-dichlorophenylamino)-2-imidazoline, 1-(benzodiox-5-oyl)-2-(2',6'-dichlorophenylamino)-2-imidazoline, 1-(benzodioxan-6-oyl)-2-(2',6'-dichlorophenylamino)-2-imidazoline, 1-(pyrid-3-oyl)-2-(2-chloro-4'-methylphenylamino)-2-imidazoline, 1-(quinolin-2-oyl)-2-(2'-chloro-4'-methyl-phenylamino)-2-imidazoline, 1-(pyrid-3-oyl)-2-(2'-chloro-4'-ethyl-phenylamino)-2-imidazoline, 1-(quinolin-2-oyl)-2-(2'-chloro-4'-ethyl-phenylamino)-2-imidazoline, 1-(pyrid-3-oyl)-2-(2'-chloro-6'-methyl-phenylamino)-2-imidazoline, 1-(quinolin-2-oyl)-2-(2'-chloro-6'-methyl-phenylamino)-2-imidazoline, 1-(pyrid-3-oyl)-2-(2'-chloro-6'-bromo-phenylamino)-2-imidazoline, 1-(quinolin-2-oyl)-2-(2'-chloro-6'-bromophenylamino)-2-imidazoline, 1-(pyrid-3-oyl)-2-(2',6'-dibromo-phenylamino)-2-imidazoline, 1-(quinolin-2-oyl)-2-(2',6'-dibromo-phenylamino)-2-imidazoline, 1-(pyrid-3-oyl)-2-(2'-chloro-3'-methyl-phenylamino)-2-imidazoline, 1-(quinolin-2-oyl)-2-(2'-chloro-3'-methyl-phenylamino)-2-imidazoline, 1-(pyrid-3-oyl)-2-(2'-methyl-5'-fluorophenylamino)-2-imidazoline, 1-(quinolin-2-oyl)-2-(2'-methyl-5'-fluorophenylamino)-2-imidazoline, 1-(isoquinolin-1-oyl)-2-(2'-methyl-5'-fluorophenylamino)-2-imidazoline, 1-(isoquinolin-3-oyl)-2-(2'-methyl-5'-fluorophenylamino)-2-imidazoline, 1-(4-methyl-quinolin-1-oyl)-2-(2'-methyl-5'-fluorophenylamino)-2-imidazoline, 1-(6-methyl-quinolin-1-oyl)-2-(2'-methyl-5'-fluorophenylamino)-2-imidazoline, 1-(7-methyl-quinolin-1-oyl)-2-(2'-methyl-5'-fluorophenylamino)-2-imidazoline, 1-(6-methoxy-quinolin-1-oyl)-2-(2'-methyl-5'-fluorophenylamino)-2-imidazoline, 1-(7-trifluoromethyl-quinolin-1-oyl)-2-(2'-methyl-5'-fluorophenylamino)-2-imidazoline, 1-(3-methyl-isoquinolin-1-oyl)-2-(2'-methyl-5'-fluorophenylamino)-2-imidazoline, 1-(5-methyl-quinolin-1-oyl)-2-(2'-methyl-5'-fluorophenylamino)-2-imidazoline, 1-(6-trifluoromethyl-quinolin-1-oyl)-2-(2'-methyl-5'-fluorophenylamino)-2-imidazoline, 1-(pyrid-3-oyl)-2-(2'-fluoro-6'-trifluoromethyl-phenylamino)-2-imidazoline and 1-(quinolin-2-oyl)-2-(2'-fluoro-6'-trifluoromethylphenylamino)-2-imidazoline.

It is to be noted that the novel compounds of the general formula I, as well as the 2-arylamino-2-imidazolines of the formula IV, may, partially or completely, be present in a second tautomeric form corresponding to the formula Ia:

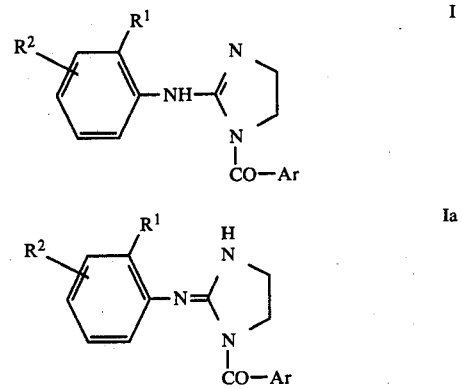

Depending on the process conditions and the starting materials, the end product is obtained either as the free base or as an addition salt with an acid.

By way of example, basic, neutral or mixed salts, as well as monohydrates, sesquihydrates or polyhydrates, can be obtained. The addition salts of the novel compounds with acids can be converted to the free base in a conventional manner, by means of basic agents, such as alkalis, or of ion exchangers. On the other hand, the free bases obtained can form salts with organic or inorganic acids. In the preparation of addition salts with acids, it is preferred to use the acids which are described in J. Pharm. Sci. 66 (1977), 1–16 and which form suitable therapeutically tolerated salts. Examples of such acids are hydrohalic acids, sulfuric acid, phosphoric acid, nitric acid, perchloric acid, aliphatic alicyclic, aromatic and heterocyclic carboxylic acids and sulfonic acids, eg. formic acid, propionic acid, succinic acid, glycolic acid, lactic acid, malic acid, tartaric acid, citric acid, ascorbic acid, maleic acid, fumaric acid, pyruvic acid, phenylacetic acid, benzoic acid, p-aminobenzoic acid, anthranilic acid, p-hydroxybenzoic acid, salicylic acid, p-aminosalicylic acid, embonic acid, methanesulfonic acid, ethanesulfonic acid, hydroxyethanesulfonic acid, ethylenesulfonic acid, halobenzenesulfonic acids, toluenesulfonic acid, naphthylsulfonic acid and sulfanilic acid, methionine, tryptophan, lysine or arginine.

These or other salts of the novel compounds, for example picrates, can serve as means of purifying the free bases obtained. For this purpose, a salt is formed with the base and is isolated from the solution, and the free base is then recovered, in a purer state, from a fresh solution of the salt.

The starting materials are known or can, should they be novel, be obtained by conventional methods.

The novel compounds and their physiologically tolerated addition salts with acids may be used as drugs, having a blood pressure-reducing action accompanied by relatively little sedative action, for the treatment of hypertonia.

The following methods were used in investigating the pharmacological properties:

1. Anti-hypertensive action

The compounds are administered orally to groups of 4–8 male spontaneously hypertonic Okamoto rats (SH rats). Before, and two hours after, the administration, the systolic blood pressure is measured on the tail of the rat by means of a piezoelectric sensor.

The ED 20% is determined, from the dose-effect relationship and taking into account the values found with untreated control animals, as the dose which lowers the systolic pressure by 20%.

2. Narcosis-prolonging action in rats

The compounds are administered orally to groups of 5 female Sprague-Dawley rats 2 hours before intraperitoneal administration of 215 mg/kg of chloral hydrate. The time at which the righting reflex ceases to function is measured. The ED 50% is determined as the dose which prolongs the period of narcosis by 50% compared to control animals which have not been pretreated.

3. Acute toxicity

To determine the acute toxicity (LD 50), the compounds are administered orally to groups of 10 male Sprague-Dawley rats each weighing 150–320 g. The period of observation is 1 week.

The reference substances were the conventional anti-hypertensive agents clonidine and benclonidine.

The novel compounds (compare Table 1) have as powerful an anti-hypertensive action as the conventional anti-hypertensive agent clonidine, when administered orally (this being the route of prime importance for therapeutic use) to spontaneously hypertonic rats. Compared to benclonidine, the novel compounds exhibit an anti-hypertensive effect at doses which are from 9.8 to 10.6 times smaller (cf. Table 1).

An undesired side-effect of clonidine is the central-suppressive (sedative) action, which was tested using, as a model, the prolongation of chloral hydrate narcosis. The doses required to prolong the narcosis are from 1.3 to 5.4 times greater than those required to lower the blood pressure. Accordingly, the ratio of the doses which respectively produce a sedative effect and an anti-hypertensive effect is substantially more advantageous, especially in the case of the compound of Example 45, than for clonidine or benclonidine.

TABLE 1

| Example No. | Anti-hypertensive effect[1] ED 20% mg/kg | R.E.[3] | Narcosis-prolonging effect[2] ED 50% mg/kg | R.E.[3] | LD 50[2] mg/kg | Q[4] |
|---|---|---|---|---|---|---|
| 1 | 0.0786 | 1.05 | 0.1 | 0.57 | 80.0 | 1.27 |
| 45 | 0.0856 | 0.97 | 0.464 | 0.12 | 44.0 | 5.42 |
| Clonidine | 0.0829 | 1.00 | 0.0565 | 1.00 | 67.3 | 0.68 |
| Benclonidine | 0.836 | 0.10 | 0.948 | 0.06 | 68.1 | 1.13 |

[1]SH rats, oral administration
[2]Rats, oral administration
[3]R.E. = relative effectiveness
[4]$Q = \frac{\text{ED 50\% for prolongation of narcosis}}{\text{ED 20\% for reduction of blood pressure}}$ The novel compounds are furthermore suitable for the treatment of migraine.

In addition, because of their effect on diastole duration and heart rate, the novel compounds may be used as drugs for the treatment of coronary heart disease.

The novel compounds may be administered orally or parenterally (subcutaneously, intravenously or intramuscularly), in a conventional manner.

The novel compounds may be employed in the conventional solid or liquid pharmaceutical forms, for example as tablets, capsules, powders, granules, dragees, suppositories or solutions. These are prepared in a conventional manner, by compounding the active compounds with the conventional pharmaceutical auxiliaries, such as tablet binders, fillers, preservatives, tablet disintegrating agents, flow regulators, plasticizers, wetting agents, dispersants, emulsifiers, solvents, retarders and/or antioxidants (cf. L. G. Goodman and A. Gilman: The Pharmacological Basis of Therapeutics). The pharmaceutical products thus obtained normally contain from 0.1 to 99 percent by weight of the active compound.

The Examples which follow illustrate the invention.

EXAMPLE 1

5.5 g (44.7 millimoles) of nicotinic acid are dissolved in 800 ml of absolute tetrahydrofuran, 7.3 g (45 millimoles) of N,N'-carbonyldiimidazole are added and the mixture is stirred for 45 minutes at room temperature. A solution of 10.3 g (44.7 millimoles) of 2-(2',6'-dichlorophenylamino)-2-imidazoline in 200 ml of absolute tetrahydrofuran is then added dropwise, with continued stirring, and the mixture is left to stand overnight at room temperature. Thereafter, the reaction solution is freed from solvent on a rotary evaporator, 200 ml of an 0.5% strength sodium bicarbonate solution are added to the residue, and the product which precipitates is filtered off and washed with water. After drying, the crude product is recrystallized from isopropanol. 7.2 g of 1-nicotinoyl-2-(2',6'-dichlorophenylamino)-2-imidazoline, melting point 173°–174° C., are obtained.

The following compounds were obtained by the method described in Example 1:

EXAMPLE 2

From furan-2-carboxylic acid and 2-(2',6'-dichlorophenylamino)-2-imidazoline:

1-(Fur-2-oyl)-2-(2',6'-dichlorophenylamino)-2-imidazoline hydrate, melting point 200.5°–201.5° C.

EXAMPLE 3

From thiophene-2-carboxylic acid and 2-(2',6'-dichlorophenylamino)-2-imidazoline:

1-(Then-2-oyl)-2-(2',6'-dichlorophenylamino)-2-imidazoline hydrochloride hydrate, melting point 179° C. (with decomposition).

EXAMPLE 4

From thiophene-3-carboxylic acid and 2-(2',6'-dichlorophenylamino)-2-imidazoline:
1-(Then-3-oyl)-2-(2',6'-dichlorophenylamino)-2-imidazoline, melting point 148°-149.5° C.

EXAMPLE 5

From pyrrole-2-carboxylic acid and 2-(2',6'-dichlorophenylamino)-2-imidazoline:
1-(Pyrroloyl)-2-(2',6'-dichlorophenylamino)-2-imidazoline, melting point 186°-188° C.

EXAMPLE 6

From N-methyl-pyrrole-2-carboxylic acid and 2-(2',6'-dichlorophenylamino)-2-imidazoline:
1-(N-Methyl-pyrrol-2-oyl)-(2',6'-dichlorophenylamino)-2-imidazoline, melting point 172°-173° C.

EXAMPLE 7

From picolinic acid and 2-(2',6'-dichlorophenylamino)-2-imidazoline:
1-Picoloyl-2-(2',6'-dichlorophenylamino)-2-imidazoline, melting point 187.5°-189° C.

EXAMPLE 8

From 6-chloronicotinic acid and 2-(2',6'-dichlorophenylamino)-2-imidazoline:
1-(6-Chloronicotinoyl)-2-(2'-6'-dichlorophenylamino)-2-imidazoline, melting point 202°-204° C.

EXAMPLE 9

From pyrazine-2-carboxylic acid and 2-(2',6'-dichlorophenylamino)-2-imidazoline:
1-(Pyrazin-2-oyl)-2-(2',6'-dichlorophenylamino)-2-imidazoline, melting point 201°-203° C.

EXAMPLE 10

From indole-2-carboxylic acid and 2-(2',6'-dichlorophenylamino)-2-imidazoline:
1-(Indol-2-oyl)-2-(2',6'-dichlorophenylamino)-2-imidazoline, melting point 247°-248° C.

EXAMPLE 11

From N-methyl-indole-2-carboxylic acid and 2-(2',6'-dichlorophenylamino)-2-imidazoline:
1-(N-Methyl-indol-2-oyl)-2-(2',6'-dichlorophenylamino)-2-imidazoline, melting point 184°-186° C.

EXAMPLE 12

From indole-3-carboxylic acid and 2-(2',6'-dichlorophenylamino)-2-imidazoline:
1-(Indol-3-oyl)-2-(2',6'-dichlorophenylamino)-2-imidazoline, melting point 261.5°-262.5° C.

EXAMPLE 13

From indole-5-carboxylic acid and 2-(2',6'dichlorophenylamino)-2-imidazoline:
1-(Indol-5-oyl)-2-(2',6'-dichlorophenylamino)-2-imidazoline, melting point 206°-207° C.

EXAMPLE 14

From quinoline-4-carboxylic acid and 2-(2',6'-dichlorophenylamino)-2-imidazoline:
1-(Quinolin-4-oyl)-2-(2',6'-dichlorophenylamino)-2-imidazoline, melting point 229°-230° C.

EXAMPLE 15

From benzodioxole-5-carboxylic acid and 2-(2',6'-dichlorophenylamino)-2-imidazoline:
1-(Benzodioxol-5-oyl)-2-(2',6'-dichlorophenylamino)-2-imidazoline, melting point 164°-165° C.

EXAMPLE 16

From 1,4-benzodioxane-6-carboxylic acid and 2-(2',6'-dichlorophenylamino)-2-imidazoline:
1-(1,4-Benzodioxan-6-oyl)-2-(2',6'-dichlorophenylamino)-2-imidazoline, melting point 184.5°-186° C.

EXAMPLE 17

From nicotinic acid and 2-(2'-chloro-6'-methylphenylamino)-2-imidazoline:
1-Nicotinoyl-2-(2'-chloro-6'-methylphenylamino)-2-imidazoline, melting point 180.5°-181° C.

EXAMPLE 18

From nicotinic acid and 2-(2',6'-dibromophenylamino)-2-imidazoline:
1-Nicotinoyl-2-(2',6'-dibromophenylamino)-2-imidazoline, melting point 192.5°-193.5° C.

EXAMPLE 19

From nicotinic acid and 2-(2'-chloro-3'-methylphenylamino)-2-imidazoline:
1-Nicotinoyl-2-(2'-chloro-3'-methylphenylamino)-2-imidazoline, melting point 196°-198° C.

EXAMPLE 20

From nicotinic acid and 2-(2',3'-dichlorophenylamino)-2-imidazoline:
1-Nicotinoyl-2-(2',3'-dichlorophenylamino)-2-imidazoline, melting point 173°-174.5° C. (the product contains 0.5 mole of isopropanol of crystallization).

EXAMPLE 21

From isonicotinic acid and 2-(2',3'-dichlorophenylamino)-2-imidazoline:
1-Isonicotinoyl-2-(2',3'-dichlorophenylamino)-2-imidazoline, melting point 152°-154° C.

EXAMPLE 22

From nicotinic acid and 2-(2'-chloro-4'-methylphenylamino)-2-imidazoline:
1-Nicotinoyl-2-(2'-chloro-4'-methylphenylamino)-2-imidazoline, melting point 151°-152° C.

EXAMPLE 23

From nicotinic acid and 2-(2'-methyl-5'-fluorophenylamino)-2-imidazoline:
1-Nicotinoyl-2-(2'-methyl-5'-fluorophenylamino)-2-imidazoline, melting point 152.5°-154° C.

EXAMPLE 24

From nicotinic acid and 2-(2',4',6'-trimethylphenylamino)-2-imidazoline:
1-Nicotinoyl-2-(2',4',6'-trimethylphenylamino)-2-imidazoline hydrate, melting point 220°-220.5° C.

EXAMPLE 25

From nicotinic acid and 2-(2',4',6'-trichlorophenylamino)-2-imidazoline:

1-Nicotinoyl-2-(2',4',6'-trichlorophenylamino)-2-imidazoline, melting point 218.5°–220° C.

EXAMPLE 26

From 3-methyl-isoxazole-5-carboxylic acid and 2-(2',6'-dichlorophenylamino)-2-imidazoline:
1-(3-Methyl-isoxazol-5-oyl)-2-(2',6'-dichlorophenylamino)-2-imidazoline, melting point 151°–153° C.

EXAMPLE 27

From 2-fluoro-isonicotinic acid and 2-(2',6'-dichlorophenylamino)-2-imidazoline;
1-(2-Fluoro-isonicotinoyl)-2-(2',6'-dichlorophenylamino)-2-imidazoline, melting point 159°–160° C.

EXAMPLE 28

From 5-fluoronicotinic acid and 2-(2',6'-dichlorophenylamino)-2-imidazoline:
1-(5-Fluoro-nicotinoyl)-2-(2',6'-dichlorophenylamino)-2-imidazoline, melting point 191°–192.5° C.

EXAMPLE 29

From 6-fluoronicotinic acid and 2-(2',6'-dichlorophenylamino)-2-imidazoline:
1-(6-Fluoro-nicotinoyl)-2-(2',6'-dichlorophenylamino)-2-imidazoline, melting point 165.5°–167° C.

EXAMPLE 30

3.15 g (22.0 millimoles) of 2-methyl-thiazole-5-carboxylic acid are dissolved in 500 ml of absolute tetrahydrofuran and 50 ml of absolute dimethylsulfoxide, 3.6 g (22.2 millimoles) of N,N'-carbonyldiimidazole are added and the mixture is stirred for 45 minutes at room temperature. A solution of 5.0 g (21.7 millimoles) of 2-(2',6'-dichlorophenylamino)-2-imidazoline in 100 ml of absolute tetrahydrofuran is then added dropwise and the mixture is stirred overnight at room temperature. The solvents are stripped off under reduced pressure on a rotary evaporator and the residue is stirred thoroughly with 100 ml of 0.5 percent strength sodium bicarbonate solution, whereupon crystallization occurs. The crystals are filtered off, washed with water and dried under reduced pressure, over a phosphorus pentoxide desiccant. 5.6 g of crude 1-(2-methylthiazol-5-oyl)-2-(2',6'-dichlorophenylamino)-2-imidazoline are obtained and are recrystallized from isopropanol, giving 2.7 g of pure product, of melting point 183°–185° C.

The following compounds were also obtained by the method described in Example 30:

EXAMPLE 31

From 2-methylnicotinic acid and 2-(2',6'-dichlorophenylamino)-2-imidazoline:
1-(2-Methyl-nicotinoyl)-2-(2',6'-dichlorophenylamino)-2-imidazoline, melting point 197°–198° C.

EXAMPLE 32

From 6-methylnicotinic acid and 2-(2',6'-dichlorophenylamino)-2-imidazoline:
1-(6-Methyl-nicotinoyl)-2-(2',6'-dichlorophenylamino)-2-imidazoline, melting point 224.5°–225.5° C.

EXAMPLE 33

From 4,6-dimethylnicotinic acid and 2-(2',6'-dichlorophenylamino)-2-imidazoline:
1-(4,6-Dimethyl-nicotinoyl)-2-(2',6'-dichlorophenylamino)-2-imidazoline, melting point 199°–201° C. (the product contains 0.5 mole of isopropanol of crystallization).

EXAMPLE 34

From isonicotinic acid N-oxide and 2-(2',6'-dichlorophenylamino)-2-imidazoline:
1-N-Oxide-isonicotinoyl)-2-(2',6'-dichlorophenylamino)-2-imidazoline, melting point 249°–250° C.

EXAMPLE 35

From 2-methylisonicotinic acid and 2-(2',6'-dichlorophenylamino)-2-imidazoline:
1-(2-Methyl-isonicotinoyl)-2-(2',6'-dichlorophenylamino)-2-imidazoline, melting point 198°–199° C.

EXAMPLE 36

From quinoline-3-carboxylic acid and 2-(2',6'-dichlorophenylamino)-2-imidazoline:
1-(Quinolin-3-oyl)-2-(2',6'-dichlorophenylamino)-2-imidazoline, melting point 207°–208° C.

EXAMPLE 37

From cinnoline-4-carboxylic acid and 2-(2',6'-dichlorophenylamino)-2-imidazoline:
1-(Cinnolin-4-oyl)-2-(2',6'-dichlorophenylamino)-2-imidazoline, melting point 202°–204° C.

EXAMPLE 38

From 6-methylpicolinic acid and 2-(2',6'-dichlorophenylamino)-2-imidazoline:
1-(6-Methylpicoloyl)-2-(2',6'-dichlorophenylamino)-2-imidazoline, melting point 159.5°–161.5° C.

EXAMPLE 39

From 4-methyl-oxazole-5-carboxylic acid and 2-(2',6'-dichlorophenylamino)-2-imidazoline:
1-(4-Methyl-oxazol-5-oyl)-2-(2',6'-dichlorophenylamino)-2-imidazoline, melting point 145.7°–147° C.

EXAMPLE 40

3.25 g (22.9 millimoles) of 6-hydroxy-nicotinic acid are dissolved in 600 ml of absolute tetrahydrofuran and 60 ml of absolute hexamethylphosphorotriamide, 3.8 g (22.9 millimoles) of N,N'-carbonyl-diimidazole are added and the mixture is stirred for 45 minutes at room temperature. A solution of 5.3 g (11.0 millimoles) of 2-(2',6'-dichlorophenylamino)-2-imidazoline in 100 ml of absolute tetrahydrofuran is then added dropwise and the mixture is left to stand overnight. The solvents are then stirred off under reduced pressure on a rotary evaporator, the residue is treated with 50 ml of 0.5% strength sodium bicarbonate solution and the mixture is decanted. 3.2 g of semi-crystalline, crude (6-hydroxynicotinoyl)-2-(2',6'-dichlorophenylamino)-2-imidazoline are obtained, which on recrystallization from isopropanol give a pure product of melting point 256°–258° C.

EXAMPLE 41

2.7 g (21.0 millimoles) of isonicotinic acid are added to 800 ml of absolute tetrahydrofuran, 4.2 g (25.9 millimoles) of N,N'-carbonyl-diimidazole are introduced and the mixture is refluxed for 2 hours. When it has cooled, a solution of 5.0 g (21.7 millimoles) of 2-(2',6'-dichlorophenylamino)-2-imidazoline in 100 ml of absolute tetrahydrofuran is added and the batch is stirred for 50 hours at room temperature. It is then freed from solvent on a rotary evaporator, the oily residue is taken up in 500 ml of tetrahydrofuran and the solution is added dropwise, with stirring, to 1.5 liters of 0.1% strength sodium bicarbonate solution. The crystals obtained (6.5 g) are recrystallized once from a 100:140 isopropanol/petroleum ether mixture and once from pure isopropanol. 3.0 g of pure 1-isonicotinoyl-2-(2',6'-dichlorophenylamino)-2-imidazoline are obtained, melting point 82.5°–83.5° C. (the product contains 0.5 mole of isopropanol of crystallization).

The following compounds were also obtained by the method described in Example 41:

EXAMPLE 42

From isonicotinic acid and 2-(2'-chloro-3'-methylphenylamino)-2-imidazoline:
1-Isonicotinoyl-2-(2'-chloro-3'-methylphenylamino)-2-imidazoline, melting point 172°–173.5° C.

EXAMPLE 43

From isonicotinic acid and 2-(2'-chloro-4'-methylphenylamino)-2-imidazoline:
1-Isonicotinoyl-2-(2'-chloro-4'-methylphenylamino)-2-imidazoline, melting point 159.5°–161° C.

EXAMPLE 44

From isonicotinic acid and 2-(2'-methyl-5'-fluorophenylamino)-2-imidazoline:
1-Isonicotinoyl-2-(2'-methyl-5'-fluorophenylamino)-2-imidazoline, melting point 170.5°–172.5° C.

EXAMPLE 45

2.85 g (16.5 millimoles) of quinoline-2-carboxylic acid are dissolved in 200 ml of absolute tetrahydrofuran, 2.7 g (16.5 millimoles) of N,N'-carbonyl-diimidazole are added and the mixture is stirred for 45 minutes at room temperature. A solution of 3.75 g (16.5 millimoles) of 2-(2',6'-dichlorophenylamino)-2-imidazoline in 75 ml of absolute tetrahydrofuran is then added dropwise and the batch is stirred overnight. Thereafter, the reaction solution is freed from solvent on a rotary evaporator and the oily residue is introduced into 200 ml of an 0.5% strength sodium bicarbonate solution. The crystalline crude product (5.2 g) is filtered off and recrystallized from N,N-dimethylacetamide/isopropanol, and the crystals are washed with cold isopropanol. 3.3 g of 1-(quinolin-2-oyl)-2-(2',6'-dichlorophenylamino)-2-imidazoline are obtained, melting point 197°–198° C.

EXAMPLE 46

1.90 g (11 millimoles) of quinoline-2-carboxylic acid are dissolved in 15 ml of absolute N,N-dimethylacetamide and 80 ml of absolute tetrahydrofuran, 3.49 g (21.5 millimoles) and N,N'-carbonyldiimidazole are added, the mixture is stirred for 45 minutes at room temperature and a solution of 2.53 g (11 millimoles) of 2-(2',6'-dichlorophenylamino)-2-imidazoline in 50 ml of absolute tetrahydrofuran is then added dropwise. Thereafter the batch is stirred for 16 hours at room temperature and is then concentrated on a rotary evaporator, the residue is taken up in about 20 ml of tetrahydrofuran, the mixture is filtered through active charcoal to remove small amounts of insoluble material and to decolorize the solution, and the filtrate is allowed to drip into 500 ml of 0.5% strength NaHCO3 solution. The crude product which precipitates is filtered off (yield, 3.7 g of material of melting point 187°–189° C.), dissolved in a small amount of dimethylacetamide and reprecipitated by dripping the solution into isopropanol. 3.0 g of pure 1-(quinolin-2-oyl)-2-(2',6'-dichlorophenylamino)-2-imidazoline of melting point 197°–198° C. are obtained; the material is identical with the product obtained according to Example 45.

EXAMPLE 47

Using the process described in Example 46, but replacing the N,N-dimethylacetamide, as co-solvent, by the same amount of N,N-dimethylformamide, 2.8 g of pure 1-(quinolin-2-oyl)-2-(2',6'-dichlorophenylamino)-2-imidazoline of melting point 197°–198° C. are obtained; the material is identical with the product obtained according to Example 45.

EXAMPLE 48

Using the process described in Example 46, but replacing the N,N-dimethylacetamide, as co-solvent, by the same amount of N-methyl-pyrrolid-2-one, 2.9 g of pure 1-(quinolin-2-oyl)-2-(2',6'-dichlorophenylamino)-2-imidazoline of melting point 197°–198° C. are obtained; the material is identical with the product obtained according to Example 45.

The following compounds were also obtained by the method described in Example 46:

EXAMPLE 49

From isoquinoline-1-carboxylic acid and 2-(2',6'-dichlorophenylamino)-2-imidazoline:
1-(Isoquinolin-1-oyl)-2-(2',6'-dichlorophenylamino)-2-imidazoline, melting point 191°–193° C.

EXAMPLE 50

From quinoline-2-carboxylic acid and 2-(2'-methyl-5'-fluorophenylamino)-2-imidazoline:
1-(Quinolin-2-oyl)-2-(2'-methyl-5'-fluorophenylamino)-2-imidazoline.

EXAMPLE 51

From 4-methylquinoline-2-carboxylic acid and 2-(2',6'-dichlorophenylamino)-2-imidazoline:
1-(4-Methyl-quinolin-2-oyl)-2-(2',6'-dichlorophenylamino)-2-imidazoline.

EXAMPLE 52

From 6-methylquinoline-2-carboxylic acid and 2-(2',6'-dichlorophenylamino)-2-imidazoline:
1-(6-Methyl-quinolin-2-oyl)-2-(2',6'-dichlorophenylamino)-2-imidazoline.

EXAMPLE 53

From 6-methoxyquinoline-2-carboxylic acid and 2-(2',6'-dichlorophenylamino)-2-imidazoline:
1-(6-Methoxy-quinolin-2-oyl)-2-(2',6'-dichlorophenylamino)-2-imidazoline.

EXAMPLE 54

From 6-fluoroquinoline-2-carboxylic acid and 2-(2',6'-dichlorophenylamino)-2-imidazoline:
1-(6-Fluoro-quinolin-2-oyl)-2-(2',6'-dichlorophenylamino)-2-imidazoline.

EXAMPLE 55

From 6-trifluoromethylquinoline-2-carboxylic acid and 2-(2',6'-dichlorophenylamino)-2-imidazoline:

1-(6-Trifluoromethyl-quinolin-2-oyl)-2-(2',6'-dichlorophenylamino)-2-imidazoline.

EXAMPLE 56

From 7-trifluoromethylquinoline-2-carboxylic acid and 2-(2',6'-dichlorophenylamino)-2-imidazoline: 1-(7-Trifluoromethyl-quinolin-2-oyl)-2-(2',6'-dichlorophenylamino)-2-imidazoline.

EXAMPLE 57

4.15 g (24 millimoles) of nicotinoylimidazolide and 4.6 g (20 millimoles) of 2-(2',6'-dichlorophenylamino)-2-imidazoline in 100 ml of absolute toluene are refluxed for 3 hours. The mixture is then concentrated to dryness on a rotary evaporator and the residue is worked up as described in Example 41. 2.9 g of pure 1-nicotinoyl-2-(2',6'-dichlorophenylamino)-2-imidazoline of melting point 172.5°–173.5° C. are obtained; the material is identical with the product obtained according to Example 1.

EXAMPLE 58

Using the process described in Example 57, 5.36 g (24 millimoles) of quinolin-2-oyl-imidazolide and 4.6 g (20 millimoles) of 2-(2',6'-dichlorophenylamino)-2-imidazoline give 6.5 g of pure 1-(quinolin-2-oyl)-2-(2',6'-dichlorophenylamino)-2-imidazoline of melting point 193.5°–196° C.; the material is identical with the product obtained according to Example 45.

EXAMPLE 59

3.40 g (50 millimoles) of imidazole are dissolved in 25 ml of absolute tetrahydrofuran, a solution of 3.54 g (25 millimoles) of nicotinoyl chloride in 25 ml of absolute tetrahydrofuran is added dropwise at room temperature, and the mixture is stirred for a further 2 hours. The imidazole hydrochloride which has precipitated is then filtered off, the filter residue is washed with a small amount of anhydrous tetrahydrofuran, the combined filtrates are added to a solution of 4.6 g (20 millimoles) of 2-(2',6'-dichlorophenylamino)-2-imidazoline in 25 ml of absolute tetrahydrofuran, and the mixture is stirred overnight. The solvent is then stripped off under reduced pressure on a rotary evaporator and the residue is twice recrystallized from isopropanol. 4.8 g of pure 1-nicotinoyl-2-(2',6'-dichlorophenylamino)-2-imidazoline of melting point 172.5°–174° C. are obtained; the material is identical with the product described in Example 1.

EXAMPLE 60

1.9 g (10 millimoles) of 1-nicotinoyl-imidazolin-2-one (melting point 191.5°–193° C.) and 1.46 g (9 millimoles) of 2,6-dichloroaniline in 30 ml of phosphorus oxychloride are stirred for 50 hours at 50° C. The excess phosphorus oxychloride is stripped off under reduced pressure on a rotary evaporator. Ice/water is added to the residue and the mixture is shaken for 30 minutes, rendered alkaline with 40% strength sodium hydroxide solution and extracted three times with chloroform. The combined organic phases are washed once with 1 N sodium hydroxide solution and then washed neutral with water, dried over sodium sulfate and concentrated to dryness under reduced pressure on a rotary evaporator. The residue is digested with hot petroleum ether and the crystalline residue is recrystallized from isopropanol. 0.87 g of pure 1-isonicotinoyl-2-(2',6'-dichlorophenylamino)-2-imidazoline of melting point 171°–173° C. are obtained; the material is identical with the product obtained according to Example 1.

EXAMPLE 61

Using the process described in Example 49, 1-(quinolin-2-oyl)-imidazolin-2-one and 2,6-dichloroaniline, in the presence of an excess of phosphorus oxychloride, give 1-(quinolin-2-oyl)-2-(2',6'-dichlorophenylamino)-2-imidazoline of melting point 196°–197.5° C.; the material is identical with the product obtained according to Example 46.

EXAMPLE 62

| Tablets containing 0.1 mg of 1-(quinolin-2-oyl)-2-(2',6'-dichlorophenylamino)-2-imidazoline: | |
|---|---|
| 1-(Quinolin-2-oyl)-2-(2',6'-dichlorophenylamino)-2-imidazoline | 0.1 mg |
| Lactose | 54.9 mg |
| Corn starch | 30 mg |
| Calcium hydrogen phosphate dihydrate | 15 mg |
| Soluble starch | 3 mg |
| Magnesium stearate | 2 mg |
| Colloidal silica | 5 mg |
| | 110 mg |

Preparation: The active compound is mixed with part of the auxiliaries, and the mixture is kneaded thoroughly with an aqueous solution of soluble starch and granulated in a conventional manner, using a sieve. The granules are mixed with the remainder of the auxiliaries and the mixture is pressed to form tablets each weighing 110 mg.

The same process can be used to prepare dragee cores, which can then be coated in a conventional manner with sugar, talc and gum arabic. The ready-mixed granules can also be filled directly into push-fit capsules.

EXAMPLE 63

| Ampoules containing 0.025 mg of 1-nicotinoyl-2-(2',6'-dichlorophenylamino)-2-imidazoline: | | |
|---|---|---|
| 1-Nicotinoyl-2-(2',6'-dichlorophenylamino)-2-imidazoline | | 0.025 mg |
| Sodium chloride | | 18 mg |
| Double distilled water | to make up to | 2.0 ml |

Preparation: The active compound and the sodium chloride are dissolved in water and the solution is sterile-filtered and filled, under nitrogen, into glass ampoules each containing 2 ml.

EXAMPLE 64

| Drops containing 0.1 mg of 1-nicotinoyl-2-(2',6'-dichlorophenylamino)-2-imidazoline per ml (=20 drops): | | |
|---|---|---|
| 1-Nicotinoyl-2-(2',6'-dichlorophenylamino)-2-imidazoline | | 0.01 g |
| Methyl p-hydroxybenzoate | | 0.07 g |
| Propyl p-hydroxybenzoate | | 0.03 g |
| Flavor correctant | | 2.0 g |
| Ethanol | | 20.0 g |
| Demineralized water | to make up to | 100 ml |

Preparation: The p-hydroxybenzoic acid esters are dissolved in ethanol and the alcohol-soluble flavor correctants (for example sodium cyclamate) are dissolved in some of the water; the two solutions are combined and the mixture is made up to 100 ml with water, clarified by filtering and filled into dropper bottles.

EXAMPLE 65

| Suppositories containing 0.4 mg of 1-(quinolin-2-oyl)-2-(2',6'-dichlorophenylamino)-2-imidazoline: | |
|---|---|
| 1-(Quinolin-2-oyl)-2-(2',6'-dichlorophenylamino)-2-imidazoline | 0.4 mg |
| Lactose | 244.6 mg |
| Suppository base (for example Witepsol H 19 and Witepsol W 45) to make up to | 1.7 g |

Preparation: The suppository base is melted and the active compound, which has been milled together with the lactose, is homogeneously dispersed in the melt at 38° C.; the mixture is cooled to 35° C. and poured into precooled suppository molds. Each suppository weighs 1.7 g.

We claim:

1. A 1-aroyl-2-phenylamino-2-imidazoline of the general formula I $$\begin{array}{c}R^2 \\ R^3\end{array} \underset{NH}{\overset{R^1}{\diagdown}} \underset{CO-Ar}{\overset{N}{\diagup}} \quad (I)$$

where
R$^1$ and R$^2$ are identical or different and each is chlorine, bromine, fluorine, methyl, ethyl, methoxy, trifluoromethyl or cyano,
R$^3$ has the meanings given for R$^1$ and R$^2$ or is hydrogen and
Ar is an unsubstituted or substituted monocyclic or bicyclic heteroaromatic radical containing 1, 2 or 3 nitrogen and/or oxygen and/or sulfur atoms, and its salts with physiologically tolerated acids.

2. A compound as claimed in claim 1, where Ar is pyrrolyl, furyl, thienyl, imidazolyl, oxazolyl, isoxazolyl, thiazolyl, isothiazolyl, oxadiazolyl, thiadiazolyl, pyridyl, pyrazinyl, indolyl, benzofuranyl, quinolinyl, isoquinolinyl, cinnolinyl, benzodioxyl or benzodioxanyl.

3. A compound as claimed in claim or 2, where Ar is substituted by one or more of the following radicals: alkyl of 1 to 4 carbon atoms, haloalkyl of 1 to 4 carbon atoms, alkoxyalkyl, where alkoxy and alkyl are each of 1 to 4 carbon atoms, halogen, hydroxyl, alkoxy of 1 to 4 carbon atoms and alkylmercapto of 1 to 4 carbon atoms.

4. A compound as claimed in claim 1, where R$^1$ is chlorine and R$^2$ is chlorine or bromine in the 6-position, methyl in the 3-, 4- or 6-position, or ethyl in the 4-position.

5. A compound as claimed in claim 1, where R$^1$ is bromine and R$^2$ is bromine in the 6-position.

6. A compound as claimed in claim 1, where R$^1$ is fluorine and R$^2$ is trifluoromethyl in the 6-position.

7. A compound as claimed in claim 1, where R$^1$ is methyl and R$^2$ is fluorine in the 5-position.

8. A compound as claimed in claim 1, where Ar is unsubstituted or substituted furyl, thienyl, thiazolyl, oxadiazolyl, pyridyl, quinolinyl, isoquinolinyl, benzodioxyl or benzodioxanyl.

9. A compound as claimed in claim 4, where Ar is unsubstituted or substituted pyrid-3-yl, isoquinolin-1-yl or quinolin-2-yl.

10. A compound selected from the group comprising 1-nicotinoyl-2-(2,6-dichlorophenylamino)-2-imidazoline, 1-(quinolin-2-oyl)-2-(2,6-dichlorophenylamino)-2-imidazoline, 1-picoloyl-2-(2',6'-dichlorophenylamino)-2-imidazoline, 1-(fur-2-oyl)-2-(2',6'-dichlorophenylamino)-2-imidazoline, 1-(2-methyl-pyrid-4-oyl)-2-(2',6'-dichlorophenylamino)-2-imidazoline, 1-nicotinoyl-2-(2'-chloro-4'-methylphenylamino)-2-imidazoline, 1-nicotinoyl-2-(2'-methyl-5'-fluorophenylamino)-2-imidazoline, 1-(isoquinolin-1-oyl)-2-(2',6'-dichlorophenylamino)-2-imidazoline, 1-(6-methylpicoloyl)-2-(2',6'-dichlorophenylamino)-2-imidazoline, 1-isonicotinoyl-2-(2',6'-dichlorophenylamino)-2-imidazoline, 1-(4-methylquinolin-2-oyl)-2-(2',6'-dichlorophenylamino)-2-imidazoline, 1-(6-methyl-quinolin-2-oyl)-2-(2',6'-dichlorophenylamino)-2-imidazoline, 1-(6-trifluoromethylquinolin-2-oyl)-2-(2',6'-dichlorophenylamino)-2-imidazoline, 1-(7-trifluoromethyl-quinolin-2-oyl)-2-(2',6'-dichlorophenylamino)-2-imidazoline, 1-(6-methoxyquinolin-2-oyl)-2-(2',6'-dichlorophenylamino)-2-imidazoline, 1-(6-fluoro-quinolin-2-oyl)-2-(2',6'-dichlorophenylamino)-2-imidazoline, 1-(7-fluoroquinolin-2-oyl)-2-(2',6'-dichlorophenylamino)-2-imidazoline, 1-(quinolin-2-oyl)-2-(2'-methyl-5'-fluorophenylamino)-2-imidazoline and its acid addition salts.

11. A compound as described in claim 1, which is 1-(quinolin-2-oyl)-2-(2,6-dichlorophenylamino)-2-imidazoline.

12. A therapeutic composition comprising a pharmaceutical excipient and an effective amount of a compound as claimed in claim 1 as the active ingredient.

13. The method of treating hypertonia in a patient suffering therefrom which comprises administering an effective amount of a compound as claimed in claim 1.

14. The method of treating hypertonia in a patient suffering therefrom, which comprises administering to said patient a composition comprising a pharmaceutically acceptable carrier or diluent and an effective amount of a compound as described in claim 11.

* * * * *